United States Patent [19]
Thomas et al.

[11] Patent Number: 5,902,590
[45] Date of Patent: May 11, 1999

[54] COSMETIC AND/OR PHARMACEUTICAL FORMULATIONS

[75] Inventors: Heike Thomas, Langenfeld; Achim Ansmann, Erkrath; Rolf Kawa, Monheim; Armin Wadle, Hilden; Reinhard Bunte, Dormagen; Udo Hees, Duisburg; Alfred Westfechtel, Hilden, all of Germany

[73] Assignee: Henkel Kommanditgesellschaft auf Aktien, Duesseldorf, Germany

[21] Appl. No.: 08/702,571

[22] PCT Filed: Feb. 22, 1995

[86] PCT No.: PCT/EP95/00633

§ 371 Date: Oct. 10, 1996

§ 102(e) Date: Oct. 10, 1996

[87] PCT Pub. No.: WO95/23586

PCT Pub. Date: Sep. 8, 1995

[30] Foreign Application Priority Data

Mar. 3, 1994 [DE] Germany ............... 44 07 015

[51] Int. Cl.$^6$ ............... C07C 69/30; C11C 3/02; A61K 6/00; A61K 7/00
[52] U.S. Cl. ............... 424/401; 514/553; 514/558; 514/724; 514/844; 514/937; 514/938; 514/939; 514/943; 554/1; 554/227
[58] Field of Search ............... 424/401; 514/844, 514/553, 558, 724, 937, 938, 939, 943; 554/227, 168, 170, 172, 1

[56] References Cited

U.S. PATENT DOCUMENTS 3,936,391  2/1976  Gabby et al. .
5,147,644  9/1992  Oppenlaender et al. .
5,424,469  6/1995  Jakobson et al. .

FOREIGN PATENT DOCUMENTS 203 831      12/1986   European Pat. Off. .
379 658       8/1990   European Pat. Off. .
451 461      10/1991   European Pat. Off. .
579 159       1/1994   European Pat. Off. .
32 34 786     3/1984   Germany .
40 05 819     8/1991   Germany .
40 23 593     1/1992   Germany .
41 00 490     3/1992   Germany .
43 09 390     9/1994   Germany .
WO94/09753    5/1994   WIPO .
WO94/18943    9/1994   WIPO .

OTHER PUBLICATIONS

Ärztl. Kosmetol, 11 (1981) pp. 101–106.
J.Soc.Cosmet.Chem 28 (1977) pp. 733–740.
Fette, Seifen, Anstrichmittel 88 (1986) pp. 101–106.
Kosmetische Färbemittel of the Farbstoffkommission der Deutschen Forschungsgemeinschaft, Verlag Chemie, Weinheim, 1984 pp. 81–106.
Lehninger, A., "Principles of Biochemistry" Worth, New York (1982), pp. 56–57.

Primary Examiner—Patricia A. Duffy
Attorney, Agent, or Firm—Ernest G. Szoke; Wayne C. Jaeschke; Real J. Grandmaison

[57] ABSTRACT

A cosmetic or pharmaceutical composition containing an emulsifier comprising an ester of palmitic acid and technical grade triglycerol with the proviso that the monoester content of the ester is from 30% to 50% by weight.

6 Claims, No Drawings

COSMETIC AND/OR PHARMACEUTICAL FORMULATIONS

BACKGROUND OF THE INVENTION

1. Field of the Invention

This invention relates to cosmetic and/or pharmaceutical formulations with increased viscosity and improved stability in storage which are distinguished by a content of selected esters of oligoglycerols with fatty acids as emulsifiers.

2. Discussion of Related Art

Emulsifiers are required for the permanent homogeneous mixing of substances which would otherwise be immiscible with one another. Esters of fatty acids with polyhydric alcohols, for example pentaerythritol, dipentaerythritol, or self-condensation products of glycerol, so-called technical oligoglycerol mixtures, are often used for this purpose in cosmetic and pharmaceutical formulations, for example for the production of cremes and notions. A review of this subject by G. Schuster and H. Pospischil was published in Ärztl. Kosmetol., 11, 30–37 (1981).

The use of polyglycerol esters as o/w emulsifiers for cosmetic formulations is described, for example, in J. Soc. Cosmet. Chem. 28, 733–740 (1977) and in Fette, Seifen, Anstrichmittel 88, 101–106 (1986).

In addition, the use of selected polyglycerol fatty acid esters as cosmetic emulsifiers is claimed in DE-A1 40 05 819 and in DE-A1 40 23 593 (BASF). However, in cases where the esters based on unsaturated or saturated fatty acids mentioned in these documents are used, it has been found that the resulting emulsions are not always sufficiently stable in storage and/or are low in viscosity, i.e. have a viscosity which is not sufficiently high, so that problem-free dosing is difficult.

Accordingly, the problem addressed by the present invention was to provide new emulsifiers based on technical oligoglycerol mixtures and fatty acids which would not have any of the disadvantages mentioned above.

DESCRIPTION OF THE INVENTION

The present invention relates to cosmetic and/or pharmaceutical formulations which are characterized in that they contain statistical monoesters of technical triglycerol with saturated $C_{16/18}$ fatty acids as emulsifiers, the monoester content being from 30 to 50% by weight.

It has surprisingly been found that the degree of self-condensation of the oligoglycerols in conjunction with the nature of the fatty acid and the percentage content of monoesters has a critical bearing on the properties of the resulting emulsifiers. The invention includes in particular the observation that the establishment of a percentage monoester content of 30 to 50% in the emulsifiers according to the invention leads to a significant improvement in storability and viscosity compared with otherwise known products of the prior art.

Triglycerol fatty acid esters

Esters of technical triglycerol with fatty acids are known substances which may be obtained by the relevant methods of preparative organic chemistry. Thus, according to the above-cited documents DE-A1 40 05 819 and DE-A1 40 23 593, technical triglycerol is esterified with fatty acids in the presence of hypophosphorous acid at 180° C. and the water of reaction is continuously distilled off from the equilibrium.

In statistical terms, the triglycerol fatty acid esters are monoesters or, more accurately, esters of—on average—1 mole of technical triglycerol with 1 mole of fatty acid. This can produce the following typical distribution:

monoesters: 30 to 50% by weight
diesters: 30 to 45% by weight
triesters: 15 to 30% by weight.

In addition, the emulsifiers may be derived from technical triglycerol with the following composition:

monoglycerol: 0 to 20% by weight
diglycerol: 10 to 35% by weight
triglycerol: 10 to 52% by weight
tetraglycerol: 5 to 25% by weight
pentaglycerol: 0 to 10% by weight
hexaglycerol: 0 to 10% by weight
oligoglycerols: 0 to 10% by weight.

Triglycerol fatty acid esters which show particularly advantageous properties in the context of the present invention are distinguished by at least one of the following two properties:

a monoester content of 30 to 50% by weight and preferably 35 to 50% by weight;
a triglycerol content of 10 to 55% by weight and preferably 35 to 55% by weight, based on the oligoglycerol content.

In addition, the emulsifiers may be derived from saturated fatty acids containing 16 to 18 carbon atoms, i.e. for example from stearic acid, tallow fatty acid and, more particularly, palmitic acid. According to the invention, particularly preferred emulsifiers are palmitic acid esters which have a monoester content of 35 to 50% by weight and a triglycerol content of 35 to 55% by weight, based on their oligoglycerol content.

The emulsifiers may be present in the cosmetic and/or pharmaceutical formulations in quantities of 0.1 to 20% by weight and preferably in quantities of 1 to 15% by weight, based on the formulation.

Cosmetic and/or pharmaceutical formulations

The formulations may contain small quantities of other surfactants compatible with the other ingredients. Typical examples are fatty alcohol sulfates, fatty alcohol polyglycol ether sulfates, monoglyceride sulfates, ether carboxylic acids, mono- and/or dialkyl sulfosuccinates, fatty acid isethionates, fatty acid sarcosinates, fatty acid taurides, alkyl and/or alkenyl oligoglucosides, alkylamidobetaines and/or protein hydrolyzates or protein fatty acid condensates of animal and particularly vegetable origin.

Other suitable auxiliaries and additives are oils, co-emulsifiers, fats and waxes, thickeners, biogenic agents, film formers, fragrances, dyes, pearlescers, preservatives and pH regulators.

Suitable oils are, for example, Guerbet alcohols based on fatty alcohols containing 6 to 18 and preferably 8 to 10 carbon atoms, esters of linear $C_{6-20}$ fatty acids with linear $C_{6-20}$ fatty alcohols, esters of branched $C_{6-13}$ carboxylic acids with linear $C_{16-18}$ fatty alcohols, esters of linear $C_{10-18}$ fatty acids with branched alcohols, more particularly 2-ethyl hexanol, esters of linear and/or branched fatty acids with dihydric alcohols and/or Guerbet alcohols, triglycerides based on $C_{6-10}$ fatty acids, vegetable oils, branched primary alcohols, substituted cyclohexanes and/or dialkyl ethers.

Suitable co-emulsifiers are both known w/o and o/w emulsifiers. Typical examples of fats are glycerides while suitable waxes include inter alia beeswax, paraffin wax or microwaxes. Suitable thickeners are, for example, crosslinked polyacrylic acids and derivatives thereof, polysaccharides, more particularly xanthan gum, guar guar, agar agar, alginates and tyloses, carboxymethyl cellulose and hydroxyethyl cellulose, also fatty alcohols, monoglycerides and fatty acids, polyacrylates, polyvinyl alcohol and polyvinyl pyrrolidone. In the context of the invention, biogenic agents are, for example, plant extracts, protein hydrolyzates and vitamin complexes. Typical film formers are, for example, polyvinyl pyrrolidone, vinyl pyrrolidone/ vinyl acetate copolymers, polymers of the acrylic acid series, quaternary cellulose derivatives and similar compounds. Suitable preservatives are, for example, formaldehyde solution, p-hydroxybenzoate or sorbic acid. Suitable pearlescers are, for example, glycol distearic acid esters, such as ethylene glycol distearate, and also fatty acids and fatty acid monoglycol esters. The dyes used may be selected from any of the substances which are permitted and suitable for cosmetic purposes, as listed for example in the publication "Kosmetische Färbemittel" of the Farbstoffkommission der Deutschen pages 81–106. These dyes are typically used in concentrations of 0.001 to 0.1% by weight, based on the mixture as a whole.

The total percentage content of auxiliaries and additives may be 1 to 50% by weight and is preferably 5 to 40% by weight, based on the formulation. The formulations may be produced in known manner, i.e. for example by hot, cold, hot-hot/cold or PIT emulsification. These are purely mechanical processes which do not involve a chemical reaction. The cosmetic and/or pharmaceutical formulations may have a water content of 25 to 95% by weight and preferably 50 to 75% by weight.

Commercial Applications

The use of the emulsifiers according to the invention leads to homogeneous cosmetic or pharmaceutical formulations of the o/w emulsion type which are stable in storage for prolonged periods, do not separate and have an advantageously high and constant viscosity.

Accordingly, the present invention also relates to the use of esters of technical oligoglycerol mixtures with an average degree of self-condensation of 2 to 4 with $C_{12-22}$ fatty acids as emulsifiers for the production of cosmetic and/or pharmaceutical formulations.

The following Examples are intended to illustrate the invention without limiting it in any way.

EXAMPLES

I. Triglycerol palmitates

The triglycerol palmitates according to the invention may be obtained in known manner by esterification of technical triglycerol mixtures with palmitic acid in the presence of alkaline catalysts. The composition of the emulsifiers according to the invention is given in Table 1. All percentages are by weight.

TABLE 1

Composition of the Emulsifiers According to the Invention

| Emul. | OLIGOGLYCEROL CONTENT | | | | | | | ESTER CONTENT | | |
| --- | --- | --- | --- | --- | --- | --- | --- | --- | --- | --- |
| | MG % | DG % | TG % | tG % | PG % | HG % | OG % | ME % | DE % | TE % |
| A1 | 18 | 27 | 21 | 14 | 9 | 4 | 7 | 39 | 33 | 28 |
| A2 | 0 | 24 | 52 | 16 | 5 | 2 | 1 | 39 | 35 | 26 |
| A3 | 18 | 27 | 21 | 14 | 9 | 4 | 7 | 44 | 34 | 22 |

Legend:
Emul. = Emulsifier
MG = Monoglycerol
DG = Diglycerol
TG = Triglycerol
tG = Tetraglycerol
PG = Pentaglycerol
HG = Hexaglycerol
OG = Oligoglycerol
ME = Monoester
DE = Diester
TE = Triester II. Performance Tests The emulsions were performance-evaluated using the basic formula according to Table 2 (percentages as % by weight):

TABLE 2

Basic Formulations

| R | c(Emuls.) % | Oil | c(Oil) % | c(GMS) % | c(H$_2$O) |
| --- | --- | --- | --- | --- | --- |
| 1 | 6 | DO | 10 | 0 | 84 |
| 2 | 3 | DO | 10 | 5 | 82 |
| 3 | 16 | CCT | 16 | 0 | 68 |
| 4 | 16 | CTI | 16 | 0 | 68 |
| 5 | 16 | P | 16 | 0 | 68 |

Legend:
Emuls. = Emulsifier
DO = Decyl oleate
CCT = $C_{8/10}$triglyceride
CTI = Cetearyl isononanoate
P = Paraffin oil
GMS = Glycerol monostearate The viscosity of the emulsions was measured after 1 week at 23 C in Brookfield RVF viscosimeter, spindle TE, 4 r.p.m., while their stability was visually evaluated after storage for 4 weeks at 20° C. and 40° C. The results are set out in Table 3:

TABLE 3

Performance Evaluation of the Emulsions

| Ex. | R | Emulsifier | Viscosity mPa · s | Stability |
|---|---|---|---|---|
| 1 | 1 | A1 | 31,250 | Stable |
| 2 | 2 | A1 | 200,000 | Stable |
| 3 | 2 | A2 | 137,500 | Stable |
| 4 | 2 | A3 | 275,000 | Stable |
| 5 | 3 | A1 | 225,000 | Stable |
| 6 | 4 | A1 | 212,500 | Stable |
| 7 | 5 | A1 | 350,000 | Stable |
| C1 | 1 | Ceteareth-12 | — | Unstable |
| C2 | 1 | Triglycerol monostearate (90% monoester) acc. to DE 40 23 593 | — | Unstable |
| C3 | 2 | Triglycerol distearate | 100,000 | Stable |
| C4 | 2 | Triglycerol monostearate (90% monoester) acc. to DE 40 23 593 | 18,750 | Unstable |
| C5 | 2 | Ceteareth-12/Ceteareth-20 (1:1) | 2,000 | Stable |
| C6 | 3 | Triglycerol monomyristate (42% monoester) | 25,000 | Unstable |
| C7 | 4 | Triglycerol monomyristate (42% monoester) | 12,500 | Unstable |
| C8 | 5 | Triglycerol monomyristate (42% monoester) | 25,000 | Unstable |

The Examples show that the change to higher monoester contents or shorter fatty acid chains leads to a significant deterioration in the performance properties of the emulsifiers.

We claim:

1. A cosmetic or pharmaceutical composition containing an emulsifier comprising an ester of palmitic acid and technical grade triglycerol wherein said technical grade triglycerol consists of 0 to 20% by weight monoglycerol, 10 to 35% by weight diglycerol, 10 to 52% by weight triglycerol, 5 to 25% by weight tetraglycerol, 0 to 10% by weight pentaglycerol, 0 to 10% by weight hexaglycerol and 0 to 10% by weight oligoglycerols, with the proviso that the monoester content of said ester is from 35 to 50% by weight, based on the total weight of said emulsifier.

2. A composition as in claim 1 wherein said emulsifier is present in an amount of 0.1% to 20% by weight, based on the weight of said composition.

3. A process for increasing the viscosity and improving the storage stability of a cosmetic or pharmaceutical composition comprising adding to said composition an emulsifier comprising an ester of palmitic acid and technical grade triglycerol wherein said technical grade triglycerol consists of 0 to 20% by weight monoglycerol, 10 to 35% by weight diglycerol, 10 to 52% by weight triglycerol, 5 to 25% by weight tetraglycerol, 0 to 10% by weight pentaglycerol, 0 to 10% by weight hexaglycerol and 0 to 10% by weight oligoglycerols, with proviso that the monoester content of said ester is from 35 to 50% by weight based on the total weight of said emulsifier.

4. A process as in claim 3 wherein said emulsifier is present in an amount of 0.1% to 20% by weight, based on the weight of said composition.

5. A cosmetic or pharmaceutical composition containing an emulsifier comprising an ester of palmitic acid and technical grade triglycerol wherein said technical grade triglycerol consists of 35% to 55% by weight triglycerol, based on the oligoglycerol content, with the proviso that the monoester content of said ester is from 35% to 50% by weight based on the total weight of the emulsifier.

6. A process for increasing the viscosity and improving the storage stability of a cosmetic or pharmaceutical composition comprising adding to said composition an emulsifier comprising an ester of palmitic acid and technical grade triglycerol wherein said technical grade triglycerol consists of 35% to 55% by weight triglycerol, based on the oligoglycerol content, with the proviso that the monoester content of said ester is from 35% to 50% by weight, based on the total weight of said emulsifier.

* * * * *